United States Patent [19]

Naka et al.

[11] Patent Number: 4,824,848

[45] Date of Patent: Apr. 25, 1989

[54] PYRAZOLO[3,4-D]PYRIMIDINE DERIVATIVES, THEIR PRODUCTION AND USE

[75] Inventors: Takehiko Naka; Yoshiyasu Furukawa; Akinobu Nagaoka, all of Hyogo, Japan

[73] Assignee: Takeda Chemical Industries, Ltd., Japan

[21] Appl. No.: 25,622

[22] Filed: Mar. 13, 1987

[30] Foreign Application Priority Data

Mar. 14, 1986 [JP] Japan .................................. 61-57920
Jan. 23, 1987 [JP] Japan .................................. 62-14627

[51] Int. Cl.$^4$ .................. A61K 31/415; C07D 487/04
[52] U.S. Cl. .................................. 514/258; 544/262; 544/301
[58] Field of Search ........................ 544/262; 514/258

[56] References Cited

U.S. PATENT DOCUMENTS 3,098,075  7/1963  Druey ................................. 544/262
4,603,203  7/1986  Furukawa .......................... 544/262

FOREIGN PATENT DOCUMENTS 166054  1/1986  European Pat. Off. ............ 544/262
50-100090  8/1975  Japan .................................. 514/258

OTHER PUBLICATIONS

Central Patents Index, Basic Abstracts Journal, Section B 32972A/18 (Japanese Patent Publication Laid Open No. 31694/1978).
T. Naka et al., Chemical and Pharmaceutical Bulletin 27(6) pp. 1328–1334, 1979.
S. Senda et al., Chemical and Pharmaceutical Bulletin 26(10) pp. 3208–3211, 1978.

*Primary Examiner*—Donald G. Daus
*Assistant Examiner*—Mark W. Noel
*Attorney, Agent, or Firm*—Wegner & Bretschneider

[57] ABSTRACT

Novel pyrazolo[3,4-d]pyrimidine derivatives represented by the general formula (I)

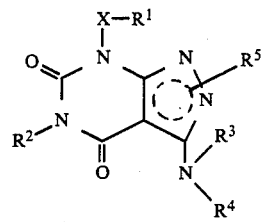

wherein
$R^1$ is an aryl or heteroaryl group which may be substituted by one to three members selected from the class consisting of halogen, $C_{1-4}$alkyl, $C_{1-4}$alkoxy, nitro, amino, N-$C_{1-4}$alkylamino, N,N-di$C_{1-4}$alkylamino, hydroxy, trifluoromethyl, carbamoyl, N-$C_{1-4}$alkylcarbamoyl and N,N-di$C_{1-4}$alkylcarbamoyl;
$R^2$ is $C_{1-4}$ alkyl;
$R^3$ and $R^4$ are independently hydrogen or $C_{1-4}$ alkyl;
$R^5$ is hydrogen, $C_{1-2}$alkyl, $C_{1-5}$alkanoyl or $C_{1-4}$alkoxycarbonyl, the group $R^5$ being attached at the 1- or 2-position of the pyrazole ring;
X is $C_{1-7}$alkylene or a group of the formula:

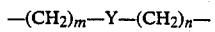

wherein m is 2 or 3,
n is an integer of 0 to 3,
and Y is oxygen, sulfur, imino or N-$C_{1-4}$alkylimino;
and the dotted line designates the presence of two double bonds in the pyrazole ring and their salts activate cerebral functions and metabolisms.

18 Claims, No Drawings

PYRAZOLO[3,4-D]PYRIMIDINE DERIVATIVES, THEIR PRODUCTION AND USE

The present invention relates to novel pyrazolo[3,4-d]pyrimidine derivatives which are useful for pharmaceuticals, their production and use.

More specifically, the present invention relates to novel pyrazolo[3,4-d]pyrimidine derivatives of the formula (I):

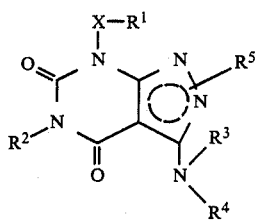

wherein $R^1$ is an aryl or hetero-aryl group which may be substituted; $R^2$ is a lower alkyl group; $R^3$ and $R^4$ are independently hydrogen or a lower alkyl group; $R^5$ is hydrogen, a lower alkyl group or a lower acyl group, the group $R^5$ being attached at the 1- or 2-position of the pyrazole ring; X is a lower alkylene group which may contain hetero-atom; and the dotted line designates the presence of two double bonds in the pyrazole ring and pharmaceutically acceptable salts thereof.

These compounds activate cerebral functions and metabolisms.

In the formula (I), the aryl group represented by $R^1$ includes phenyl, naphthyl, etc., preferably phenyl. The aryl group may be optionally substituted with 1 to 3 substituents, for example, halogen (e.g. fluorine, chlorine, bromine), lower ($C_{1-4}$) alkyl (e.g. methyl, ethyl), lower ($C_{1-4}$) alkoxy (e.g. methoxy, ethoxy), nitro, amino, N-lower ($C_{1-4}$) alkylamino (e.g. methylamino), N,N-di-lower ($C_{1-4}$) alkylamino (e.g. dimethylamino), hydroxy, trifluoromethyl, carbamoyl, N-lower ($C_{1-4}$) alkyl carbamoyl (e.g. N-methyl carbamoyl), N,N-di-lower ($C_{1-4}$) alkyl carbamoyl (e.g. N,N-dimethyl carbamoyl), etc. Among these substituents, are preferable halogen, lower alkyl, lower alkoxy, nitro and amino, more preferably halogen and nitro. The position at which the substitution occurs is not especially limited, but it may be any of ortho-, meta- and para-position, and when the substituent is halogen, metal-position is preferable.

The hetero-aryl group represented by $R^1$ includes mono- or di-cyclic hetero-aryl containing 1 to 3 oxygen atoms, sulfur atoms and nitrogen atoms, for example, cinnolinyl, furyl, isobenzofuranyl, isothiazolyl, isoxazolyl, naphthyridinyl, phthalazinyl, pyrazinyl, pyridazinyl, pyridyl, pyrimidinyl, quinazolinyl, quinolyl, quinoxalinyl, thienyl, pyridinio, quinazolinio, quinolino, quinoxalinio, etc. As the mono-cyclic hetero-aryl is preferable 5- or 6-membered hetero-aryl, and as the di-cyclic hetero-aryl is preferable condensed hetero-aryl between 5- or 6-membered hetero-aryl and benzene ring. Among the hetero-aryl groups are preferable pyridyl and thienyl. These hetero-aryl groups may be optionally substituted with the same substituents as the above aryl groups'.

The lower alkyl group represented by $R^2$ includes $C_{1-4}$ alkyl such as methyl, ethyl, propyl, isopropyl, butyl, isobutyl, sec-butyl, tert-butyl, etc., and among them is preferable propyl.

The lower alkyl group shown by $R^3$ and $R^4$ includes $C_{1-4}$ alkyl such as methyl, ethyl, propyl, isopropyl, butyl, isobutyl, sec-butyl, tert-butyl, etc. Among the compounds (I) are preferable those were $R^3$ is a lower alkyl group and $R^4$ is hydrogen, more preferably those where $R^3$ is methyl or ethyl and $R^4$ is hydrogen.

As the lower alkyl group represented by $R^5$ are preferable $C_{1-2}$ alkyl (e.g. methyl, ethyl).

The acyl group represented by $R^5$ includes lower ($C_{1-5}$) alkanoyl such as acetyl, propionyl, butyryl, etc. and lower ($C_{1-4}$) alkoxy carbonyl such as methoxy carbonyl, ethoxy carbonyl, etc.

The lower alkylene group represented by X includes $C_{1-7}$ straight-chain alkylene such as methylene, ethylene, trimethylene, tetramethylene, pentamethylene, hexamethylene, etc. and $C_{2-7}$ branched alkylene such as ethylidene, propylene, ethylethylene, etc. and among them are preferable methylene and ethylene and methylene is especially preferred.

The lower alkylene group containing a hetero-atom represented by X includes groups represented by the formula: $-(CH_2)_m-Y-(CH_2)_n-$ wherein m is 2 or 3, n is an integer of 0 to 3 and Y is oxygen, sulfur, imino or N-lower ($C_{1-4}$) alkylimino, etc.

Among the above-mentioned compounds are more preferable such compounds (I) wherein $R^1$ is optionally substituted phenyl (more preferably m-chlorophenyl), $R^2$ is $C_{3-4}$ alkyl (more preferably propyl), $R^3$ and $R^4$ are each hydrogen or $C_{1-2}$ alkyl (more preferably $R^3$ is methyl, $R^4$ is hydrogen), $R^5$ is hydrogen or $C_{2-4}$ alkanoyl attached at the 2-position of the pyrazole ring (more preferably hydrogen) and X is methylene or ethylene (more preferably methylene).

The preferred pharmaceutically acceptable salts of the compound (I) are pharmaceutically acceptable acid addition salts, for example, inorganic acid salts such as hydrochlorides, hydrobromides, sulfates, nitrates, phosphates, etc., and organic acid salts such as acetates, tartrates, citrates, fumarates, maleates, etc.

In cases in which $R^1$ is a hetero-aryl group which has the quaternary nitrogen, such as pyridinio, quinazolinio, quinolinio, quinoxalinio, the compound (I) may form salts with pharmaceutically acceptable anions such as inorganic acid anions (e.g. chloride ion, sulfate ion, nitrate ion, phosphate ion, etc.) and organic acid anions (e.g. acetate ion, tartrate ion, citrate ion, fumarate ion, maleate ion, etc.).

The said salts with pharmaceutically acceptable anions fall within the scope of the present invention.

The compound represented by the formula (I) can be produced by, for example, the following four kinds of processes which comprises: (a) reacting a compound of the formula (II):

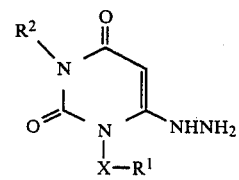

wherein $R^1$, $R^2$ and X are as defined above with a compound of the formula: $R^3-NCS$ wherein $R^3$ is as defined above, to produce a compound of the formula (Ia):

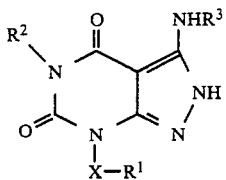

and, if desired, reacting the compound of the formula (Ia) with an alkylating agent or an acylating agent to produce a compound of the formula (I) wherein $R^5$ is a lower alkyl group or a lower acyl group or (b) heating a compound of the formula (III):

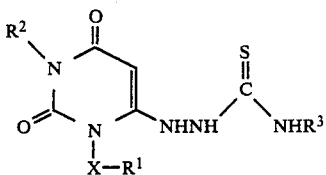

wherein $R^1$, $R^2$, $R^3$ and X are as defined above to produce the compound of the formula (Ia)

and, if desired, reacting the compound of the formula (Ia) with an alkylating agent or an acylating agent to produce a compound of the formula (I) wherein $R^5$ is a lower alkyl group or a lower acyl group or (c) reacting the compound of the formula (II) with a compound of the formula:

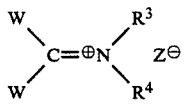

wherein $R^3$ and $R^4$ are lower alkyl group and W and Z are halogen, to produce a compound of the formula (Ib):

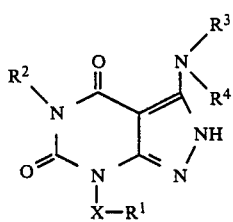

and, if desired, reacting the compound of the formula (Ib) with an alkylating agent or an acylating agent to produce a compound of the formula (I) wherein $R^5$ is a lower alkyl group or a lower acyl group or (d) reacting a compound of the formula (V):

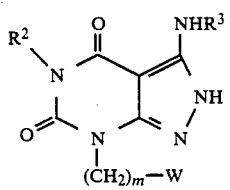

wherein $R^2$, $R^3$ and W are as defined above and m is 2 or 3 with a compound of the formula:

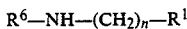

wherein $R^1$ is as defined above, n is an integer of 0 to 3 and $R^6$ is hydrogen or a lower alkyl group or a compound of the formula: $HS-(CH_2)_n-R^1$ or a compound of the formula: $HO-(CH_2)_n-R^1$ to produce a compound of the formula (If):

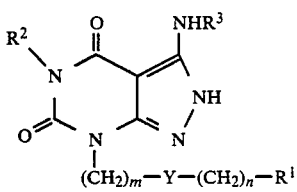

wherein Y is oxygen, sulfur, imino or N—$C_{1-4}$alkylimino and, if desired, reacting the compound of the formula (If) with an alkylating agent or an acylating agent to produce a compound of the formula (I) wherein $R^5$ is a lower alkyl group or a lower acyl group.

The reaction of the compound (II) with isothiocyanates ($R^3$—NCS) in the process (a) above is desirably carried out with use of about 1 to 5 moles of isothiocyanates ($R^3$—NCS) per mole of the compound (II) in a solvent such as dimethylformamide, pyridine, dimethyl acetamide, dimethyl sulfoxide, etc. The reaction is preferably carried out at about 50° C.–130° C. and for about 3–40 hours. The reaction is more preferably carried out initially at about 50° C.–70° C. for about 1–3 hours than at about 90° C.–130° C. for about 3–40 hours. The reaction product is readily obtained as crystals by adding alcohols (e.g. methanol or ethanol, etc.) or water-containing alcohol to the reaction solution, after completion of the reaction.

The reaction from the compound (III) to the compound (Ia) in the process (b) is carried out by subjecting the compound (III) to heating, desirably in a solvent such as dimethylformamide, dimethyl acetamide, pyridine, dimethyl sulfoxide, etc. The reaction is carried out advantageously at about 50° C.–130° C. for about 3–40 hours. The reaction product can be obtained in a manner similar to that mentioned above.

The reaction of the compound (II) with the compound of the formula:

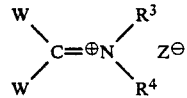

in the process (c) is advantageously conducted by allowing the compound (II) to react with, for example, phosgene iminium chloride in a solvent such as chloroform, methylene chloride, etc. at 10° C. to refluxing temperature for 1–5 hours. The reaction product can be obtained in a manner similar to that mentioned above.

The reaction from the compound (V) with the nucleophilic reagent exemplified by amines ($R^6$—N-H—$(CH_2)_n$—$R^1$), alcohols (HO—$(CH_2)_n$—$R^1$) or thiols (HS—$(CH_2)_n$—$R^1$) in the process (d) is desirably carried out in a conventional organic solvent (e.g. ethers such as dioxane or tetrahydrofuran, etc., ketones such as acetone or methylethylketone, etc.), at 10° C. to refluxing temperature for 5-20 hours. This reaction may be carried out in the co-presence of a conventional basic catalyst. The reaction product can be obtained as crystals by adding aqueous alcohol, etc. to the reaction solution. In case of an amino-substituted compound, it can be easily obtained as crystals by having it extracted in an aqueous layer as hydrochloride, followed by neutralization with alkali.

If desired, the compound (Ia), (Ib) or (If) produced in the processes (a) to (d) is reacted with an alkylating agent or an acylating agent to produce the compound (I) wherein $R^5$ is a lower alkyl group or a lower acyl group as shown by the following reaction scheme:

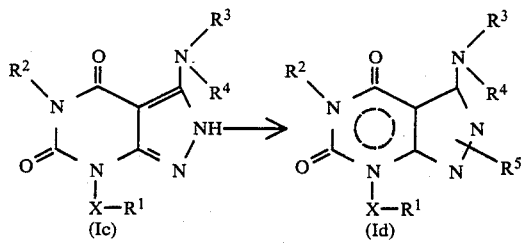

wherein $R^1$, $R^2$ and X are as defined above, $R^3$ and $R^4$ are independently hydrogen or a lower alkyl group and $R^5$ is a lower alkyl group or a lower acyl group.

As the alkylating agent, there may be used, for example, alkyl halides and as the acylating agent, there may be used acid anhydrides, acid halides or alkyl halogeno carbonate. These reagents are used in quantities within the range of about 1-5 moles per mole of the compound (Ia), (Ib) or (If) and are advantageously allowed to undergo reaction in the presence of an acid acceptor agent. Examples of the acid acceptor agent include potassium carbonate, sodium carbonate, triethylamine, pyridine, etc., and the reaction is desirably carried out at about 10° C.-100° C. for about 1-10 hours in a solvent such as pyridine, dimethylformamide, acetonitrile, etc.

Pharmaceutically acceptable salts of the compound (I) can be formed, depending on cases by the reaction for producing the compound (I), and can be also obtained by adding pharmaceutically acceptable acids to the compound (I) by per se known methods.

Among the starting compounds, the compounds (II) and (III) are novel compounds, which can be prepared by, for example, the following method.

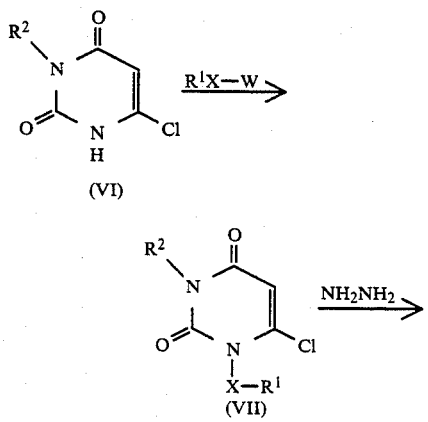

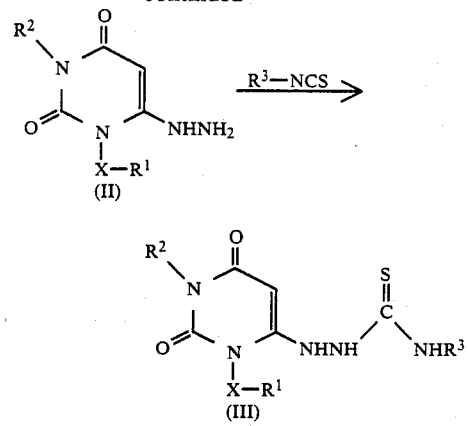

wherein $R^1$, $R^2$, $R^3$, X and W are as defined above.

The reaction (f) comprises allowing a compound (VI) synthesized after the manner described on Ann. Chem. 691, 142 (1966) or Chem. Ber. 95, 1597 (1962) to react with an alkylating agent in a conventional organic solvent (e.g. dimethylformamide or acetonitrile) in the presence of an inorganic base such as potassium carbonate, sodium carbonate, etc., advantageously at about 10° C.-100° C. for about 2-20 hours. As the alkylating agent, there may be used bromide, chloride, etc. or iodide by pre-treatment with sodium iodide, etc. The reaction of the compound (VII) with hydrazine which may contain water is carried out in a conventional organic solvent (e.g. ethanol or methanol), advantageously at about 10° C. to refluxing temperature for about 1-3 hours. The reaction of the compound (II) with isothiocyanate ($R^3$NCS) is desirably carried out in a conventional solvent (e.g. dimethylformamide, pyridine, acetonitrile, etc). at 10° C.-60° C. for about 1-5 hours. The compounds (VII), (II) and (III) can be be readily isolated and purified by the usual manner.

The starting compound (V) can be prepared by, for example, the following method.

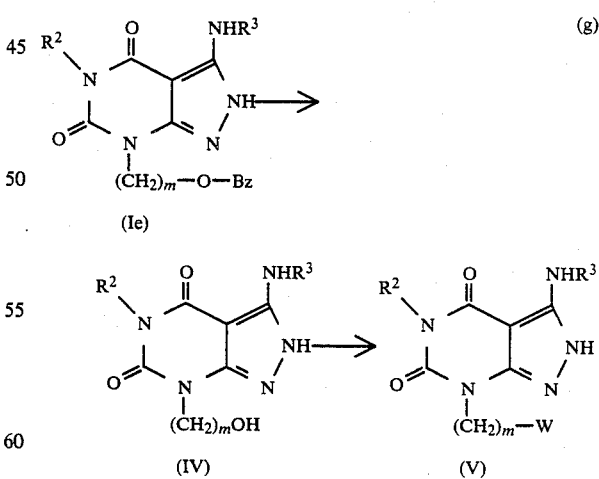

The reaction (g) is to obtain the compound (V) by subjecting the compound (Ie) obtained by the reaction in the process (a) or (b) to de-benzylation, then by leading the resultant compound (IV) to the compound (V) with a halogenating agent. As a method of the de-benzylation, are employable hydrogenolysis method, trimethylsilyl iodide method, hydrobromic acid method, etc. The hydrogenolysis method is desirably carried out under an atmosphere of hydrogen in the presence of a suitable catalyst (e.g. palladium carbon, etc.) at about 10° C.-80° C. under normal or elevated pressure in a solvent such as alcohol, etc. The trimethylsilyl iodide method is desirably carried out by adding trimethylsilyl iodide at room temperature in a solvent e.g. acetonitrile, etc., then by allowing the reaction to proceed at about 10° C.-80° C. for 1-20 hours. Or, it is also desirable to suspend the compound (Ie) and sodium iodide in acetonitrile, to add dropwise to the suspension trimethylsilyl chloride at room temperature and to allow the reaction to proceed at about 10° C.-80° C. for 1-20 hours. The halogenation of the resultant alcohol is preferably conducted by employing thionyl chloride or phosphorous oxychloride, etc., as the halogenating agent, in a conventional organic solvent such as chloroform or methylene chloride, etc. in the presence of a basic catalyst (e.g. pyridine or triethylamine, etc.) at 10° C. to refluxing temperature for about 1-5 hours. The compound (V) can be readily isolated and purified by the usual manner.

The pyrazolo[3,4-d]pyrimidine derivatives of the formula (I) and their salts of the present invention are useful, owing to their properties of activating cerebral functions and metabolism, for the therapy and prophylaxis, to mammals inclusive of humans, or neurosis and mental diseases including dementia caused by cerebral apoplexy, head trauma or encephalatrophic diseases (Alzheimer's disease, etc.), and they can be used for the prophylaxis and therapy of, for example, amnesia, retention disturbance, disorientation, emotional incontinence, hypobulia and dystropy.

The compounds (I) are of low toxicity [$LD_{50}$ (p.o): >1000 mg/kg body weight (rat)]. When the compounds (I) are used as drugs mentioned as above, they can be safely administered orally or non-orally as such or in admixture with suitable, pharmaceutically acceptable carriers, excipients or diluents in such dosage form of powder, granules, tablets, capsules, injections, suppositories, ointments and so forth. The dose of the compounds (I) varies with the kinds of disease, condition or symptom, subject, route of administration, etc. Generally, however, it is preferable to administer the compounds (I) in a single dose in the range of about 1-50 mg/kg (body weight), about 1-3 times daily, more preferably about 1-20 mg/kg (body weight), about 1-3 times daily.

The following reference examples, examples, formulation examples and experiments are intended to illustrate the present invention in further detail and should by no means be construed as limiting the scope of the present invention.

Reference Example-1

3-Butyl-6-hydrazino-1-(4-methoxybenzyl)uracil

To a mixture of 3-butyl-6-chlorouracil (5.0 g, 24.6 mM), potassium carbonate (4.4 g, 32 mM) and potassium iodide (0.17 g, 1 mM) in dimethylformamide [DMF] (50 ml) was added 4-methoxybenzyl chloride (4.65 ml, 32 mM). The mixture was stirred at room temperature for 5 hours and was then concentrated under reduced pressure, and the resulting residue was diluted with water (50 ml) and extracted with chloroform (100 ml). The organic layer was washed with water, dried ($MgSO_4$), and concentrated to dryness to give a brown syrup. The syrup was purified by flash chromatography on silica gel (elution with chloroform) to give 3-butyl-6-chloro-1-(4-methoxybenzyl)uracil as an oil. To a solution of the oil in ethanol (50 ml) was added hydrazine hydrate (20 ml) and the mixture was stirred at room temperature for 2 hours. The solution was concentrated under reduced pressure to give crude crystals, which were recrystallized from 70% ethanol to give pale yellow crystals (4.23 g, 54%), m.p. 167°-170° C.

Elemental Analysis for $C_{16}H_{22}N_4O_3$:

|  | C (%) | H (%) | N (%) |
|---|---|---|---|
| Calcd.: | 60.36; | 6.97; | 17.60 |
| Found: | 60.48; | 6.88; | 17.51 |

The following compounds were obtained by the same procedure.

| Reference Example | —X—R$^1$ | R$^2$ | m.p. (°C.) | Yield (%) |
|---|---|---|---|---|
| 1 | —CH$_2$—⟨C$_6$H$_4$⟩—OMe | Bu | 167-170 | 54 |
| 2 | —CH$_2$—⟨C$_6$H$_4$⟩—Me | Et | 170-172 | 69 |
| 3 | —CH$_2$—⟨C$_6$H$_4$⟩ (2-Cl) | Pr | 193-196 | 50 |
| 4 | —CH$_2$—⟨C$_6$H$_4$⟩ (3-Cl) | Pr | 135-137 | 76 |
| 5 | —CH$_2$—⟨C$_6$H$_4$⟩—Cl | Pr | 205-208 | 78 |
| 6 | —CH$_2$—(pyridyl) | Pr | 95-98 | 64 |
| 7 | —CH$_2$—(pyridyl) | Pr | 110-113 | 32 |

-continued

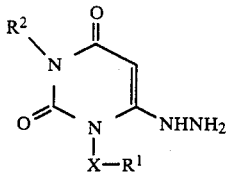

| Reference Example | —X—R¹ | R² | m.p. (°C.) | Yield (%) |
|---|---|---|---|---|
| 8 | —CH₂—(thiophene) | Pr | 193–195 | 72 |
| 9 | —CH₂CH₂—(phenyl) | Pr | 133–135 | 59 |
| 10 | —CH₂CH₂OCH₂—(phenyl) | Pr | 120–122 | 84 |
| 11 | —CH₂—(phenyl) | Bu | 175–177 | 66 |
| 12 | —CH₂—(phenyl)—Cl | Bu | 173–175 | 73 |
| 13 | —CH₂—(phenyl with O₂N) | Bu | 185–190 | 44 |
| 14 | —CH₂—(phenyl)—NO₂ | Bu | 147–149 | 54 |

In the above Table, Me, Et, Pr and Bu represent methyl, ethyl, propyl and butyl, respectively.

Reference Example-15

1-(3-Chlorobenzyl)-6-(4-methylthiosemicarbazide)-3-propyluracil

A solution of 1-(3-chlorobenzyl)-6-hydrazino-3-propyluracil (4.0 g, 13 mM) and methyl isothiocyanate (1.16 ml, 17 mM) in dimethylformamide [DMF] (15 ml) was stirred at 50° C. for 5 hours. The solution was concentrated to dryness to give a crystalline product. Recrystallization from DMF/methanol/water gave colorless crystals (4.15 g, 84%), m.p. 221°–223° C.

Elemental Analysis for $C_{16}H_{20}ClN_5O_2S$:

|  | C (%) | H (%) | N (%) |
|---|---|---|---|
| Calcd.: | 50.32; | 5.28; | 18.34 |
| Found: | 50.61; | 5.30; | 18.19 |

Reference Example-16

5-Butyl-7-(2-hydroxyethyl)-3-methylaminopyrazolo[3,4-d]pyrimidine-4,6(5H,7H)-dione To a mixture of 7-(2-benzyloxyethyl)-5-butyl-3-methylaminopyrazolo[3,4-d]pyrimidine-4,6(5H,7H)-dione (1.0 g, 2.7 mM) and sodium iodide (3 g, 20 mM) in acetonitrile (20 ml) was added dropwise trimethylsilyl chloride (2.6 g, 20 mM) at room temperature. The mixture was stirred at room temperature for 2 hours and poured onto ice-water to give crystals. Recrystallization from DMF/methanol/water gave pale yellow crystals (0.3 g, 40%), m.p. 248°–253° C.

Elemental Analysis for $C_{12}H_{19}N_5O_3$:

|  | C (%) | H (%) | N (%) |
|---|---|---|---|
| Calcd.: | 51.23; | 6.81; | 24.90 |
| Found: | 51.09; | 6.93; | 24.71 |

Reference Example-17

5-Butyl-7-(2-chloroethyl)-3-methylaminopyrazolo[3,4-d]pyrimidine-4,6(5H,7H)-dione.

To a suspension of 5-butyl-7-(2-hydroxyethyl)-3-methylaminopyrazolo[3,4-d]pyrimidine-4,6(5H,7H)-dione (2.5 g, 8.9 mM) in chloroform (30 ml) and pyridine (4 ml, 50 mM) was added thionyl chloride (3,7 ml, 50 mM) at room temperature. The solution was refluxed for 2 hours and concentrated to dryness under reduced pressure to give a syrup. The syrup was poured onto ice-water to give colorless powder. Recrystallization from DMF/methanol/water gave colorless crystals (2.5 g, 94%), m.p. 270°–272° C.

Elemental Analysis for $C_{12}H_{18}ClN_5O_2$:

|  | C (%) | H (%) | N (%) |
|---|---|---|---|
| Calcd.: | 48.08; | 6.05; | 23.36 |
| Found: | 48.21; | 5.82; | 23.39 |

Example-1

5-Ethyl-3-methylamino-7-(4-methylbenzyl)-pyrazolo[3,4-d]pyrimidine-4,6(5H,7H)-dione A solution of 3-ethyl-6-hydroazino-1-(4-methylbenzyl)-uracil (5 g, 18 mM) and methyl isothiocyanate (3,7 ml, 55 mM) in DMF (50 ml) was stirred at 90° C. for 14 hours and then at 110° C. for additional 14 hours. After addition of water (10 ml), the solution was cooled to give crystals.

Recrystallization from DMF/ethanol/water gave colorless needles (4.49 g, 79%), m.p. >300° C.

Elemental Analysis for $C_{16}H_{19}N_5O_2$:

|  | C (%) | H (%) | N (%) |
|---|---|---|---|
| Calcd.: | 61.33; | 6.11; | 22.35 |
| Found: | 61.29; | 5.93; | 22.17 |

Example-2

5-Ethyl-2-methyl-3-methylamino-7-(4-methylbenzyl)-2H-pyrazolo[3,4-d]pyrimidine-4,6(5H,7H)-dione A mixture of 5-ethyl-3-methylamino-7-(4-methylbenzyl)-2H-pyrazolo[3,4-d]pyrimidine-4,6(5H,7H)-dione (0.5 g, 1.6 mM), methyl iodide (0,46 g, 3.2 mM) and potassium carbonate (0,45 g, 3.2 mM) in DMF (8 ml) was stirred at 60° C. for 30 hours.

The reaction mixture was concentrated under reduced pressure. The crude product was purified by chromatography on silica gel (15 g, chloroform) to give crystals. Recrystallization from 70% ethanol afforded colorless needles (0.28 g, 54%), m.p. 175°–176° C.

Elemental Analysis for $C_{17}H_{21}N_5O_2$:

|  | C (%) | H (%) | N (%) |
| --- | --- | --- | --- |
| Calcd.: | 62.37; | 6.47; | 21.39 |
| Found: | 62.29; | 6.39; | 21.51 |

Example-3

2-Acetyl-5-ethyl-3-methylamino-7-(4-methylbenzyl)-2H-pyrazolo[3,4-d]pyrimidine-4,6(5H,7H)-dione A mixture of 5-ethyl-3-methylamino-7-(4-methylbenzyl)-pyrazolo[3,4-d]pyrimidine-4,6(5H,7H)-dione (0.5 g, 1.6 mM) and acetic anhydride (0.33 g, 3,2 mM) in pyridine (5 ml) was stirred at 60° C. for 18 hours.

The reaction solution was concentrated to dryness and the residue was purified by chromatography on silica gel (15 g, chloroform). Recrystallization from acetone/isopropyl ether gave colorless needles (0,43 g, 76%), m.p. 185°–187° C.

Elemental Analysis for $C_{18}H_{21}N_5O_3$:

|  | C (%) | H (%) | N (%) |
| --- | --- | --- | --- |
| Calcd.: | 60.83; | 5.96; | 19.71 |
| Found: | 61.06; | 5.98; | 19.52 |

Example-4

7-Benzyl-3-methylamino-5-propylpyrazolo[3,4-d]pyrimidine-4,6(5H,7H)-dione

A solution of 1-benzyl-6-hydrazino-3-propyluracil (2.0 g, 7.3 mM) and methyl isothiocyanate (1.5 ml, 22 mM) in DMF (20 ml) was stirred at 120° C. for 20 hours. Ethanol (20 ml) was added to the solution, which was cooled to give crystals. Recrystallization from DMF/ethanol gave colorless needles (1.6 g, 70%), m.p. 307°–310° C.

Elemental Analysis for $C_{16}H_{19}N_5O_2$:

|  | C (%) | H (%) | N (%) |
| --- | --- | --- | --- |
| Calcd.: | 61.33; | 6.11; | 22.35 |
| Found: | 61.40; | 6.02; | 22.25 |

Example-5

7-(2-Chlorobenzyl)-3-methylamino-5-propylpyrazolo[3,4-d]pyrimidine-4,6(5H,7H)-dione A solution of 1-(2-chlorobenzyl)-6-hydrozino-3-propyluracil (1.33 g, 4.3 mM) and methyl isothiocyanate (0.9 ml, 12.9 mM) in DMF (20 ml) was heated at 120° C. for 20 hours. Methanol (10 ml) was added to the solution, which was cooled to give crystals. Recrystallization from DMF/methanol afforded colorless crystals (0.64 g, 42%), m.p. >300° C.

Elemental Analysis for $C_{16}H_{18}ClN_5O_2$:

|  | C (%) | H (%) | N (%) |
| --- | --- | --- | --- |
| Calcd.: | 55.25; | 5.22; | 20.14 |
| Found: | 55.53; | 5.42; | 20.03 |

Example-6

7-(3-Chlorobenzyl)-3-methylamino-5-propylpyrazolo[3,4-d]pyrimidine-4,6(5H,7H)-dione A solution of 1-(3-chlorobenzyl)-6-hydrazino-3-propyluracil (3.0 g, 9.6 mM) and methyl isothiocyanate (2.2 ml, 32 mM) in DMF (30 ml) was heated at 120° C. for 27 hours. To the solution was added 50% methanol (10 ml) and the mixture was cooled to give crystals. Recrystallization from DMF/methanol afforded colorless crystals (1.22 g, 36%), m.p. 263°–265° C.

Elemental Analysis for $C_{16}H_{18}ClN_5O_2$:

|  | C (%) | H (%) | N (%) |
| --- | --- | --- | --- |
| Calcd.: | 55.25; | 5.22; | 20.14 |
| Found: | 55.34; | 5.31; | 20.12 |

Example-7

7-(3-Chlorobenzyl)-3-methylamino-5-propylpyrazolo[3,4-d]pyrimidine-4,6(5H,7H)-dione A solution of 1-(3-chlorobenzyl)-6-(4-methylthiosemicarbazido)-3-propyluracil (3.81 g, 10 mM) in DMF (40 ml) was stirred at 100° C. for 20 hours. To the reaction solution was added 50% methanol (20 ml) and the mixture was cooled to give crystals. Recrystallization from DMF/methanol gave colorless crystals (2.49 g, 72%), m.p. 263°–265° C.

Elemental Analysis for $C_{16}H_{18}ClN_5O_2$:

|  | C (%) | H (%) | N (%) |
| --- | --- | --- | --- |
| Calcd.: | 55.25; | 5.22; | 20.14 |
| Found: | 55.29; | 5.18; | 20.13 |

Example-8

7-(4-Chlorobenzyl)-3-methylamino-5-propylpyrazolo[3,4-d]pyrimidine-4,6(5H,7H)-dione A solution of 1-(4-chlorobenzyl)-6-(4-methylthiosemicarbazido)-3-propyluracil (4.8 g, 12.6 mM) in DMF (50 ml) was stirred at 100° C. for 40 hours. To the solution was added 50% methanol (20 ml) and the mixture was cooled to give crystals. Recrystallization from DMF/methanol gave colorless crystals (2.8 g, 50%), m.p. 305°–307° C.

Elemental Analysis for $C_{16}H_{18}ClN_5O_2$:

|  | C (%) | H (%) | N (%) |
| --- | --- | --- | --- |
| Calcd.: | 55.25; | 5.22; | 20.14 |
| Found: | 55.21; | 5.25; | 20.23 |

Example-9

7-(4-Fluorobenzyl)-3-methylamino-5-propyl-pyrazolo[3,4-d]pyrimidine-4,6(5H,7H)-dione A solution of 1-(4-fluorobenzyl)-6-hydrazino-3-propyluracil (1.5 g, 5.1 mM) and methyl isothiocyanate (1.2 ml, 17 mM) in DMF (20 ml) was heated at 120° C. for 24 hours. To the solution was added 50% methanol (10 ml) and the mixture was cooled to give crystals. Recrystallization from DMF/methanol/water gave pale yellow crystals (0.62 g, 36%), m.p. 262°–265° C.

Elemental Analysis for $C_{16}H_{18}FN_5O_2$:

|  | C (%) | H (%) | N (%) |
| --- | --- | --- | --- |
| Calcd.: | 58.00; | 5.48; | 21.14 |
| Found: | 57.73; | 5.37; | 21.39 |

Example-10

7-(4-Bromobenzyl)-3-methylamino-5-propyl-pyrazolo[3,4-d]pyrimidine-4,6(5H,7H)-dione A solution of 1-(4-bromobenzyl)-6-hydrazino-3-propyluracil (4.15 g, 11.8 mM) and methyl isothiocyanate (2.7 ml, 40 mM) in DMF (50 ml) was heated at 120° C. for 24 hours. To the reaction solution was added 50% methanol (15 ml) and the mixture was cooled to give crystals. Recrystallization from DMF/methanol gave colorless needles (2.19 g, 47%), m.p. 308°–310° C.

Elemental Analysis for $C_{16}H_{18}BrN_5O_2$:

|  | C (%) | H (%) | N (%) |
| --- | --- | --- | --- |
| Calcd.: | 48.99; | 4.63; | 17.85 |
| Found: | 48.59; | 4.52; | 17.98 |

Example-11

3-Methylamino-7-(4-pyridylmethyl)-5-propyl-pyrazolo[3,4-d]pyrimidine-4,6(5H,7H)-dione A solution of 6-hydrazino-1-(4-pyridylmethyl)-3-propyluracil (1.5 g, 5.7 mM) and methyl isothiocyanate (1.55 ml, 23 mM) in DMF (15 ml) was heated at 90° C. for 14 hours and then at 110° C. for 14 hours. To the reaction solution was added 50% methanol (10 ml) and the mixture was cooled to give crystals. Recrystallization from DMF/ethanol/water afforded colorless needles (1.02 g, 57%), m.p. >300° C.

Elemental Analysis for $C_{15}H_{18}N_6O_2$:

|  | C (%) | H (%) | N (%) |
| --- | --- | --- | --- |
| Calcd.: | 57.31; | 5.77; | 26.73 |
| Found: | 57.16; | 5.57; | 26.50 |

Example-12

3-Methylamino-7-(3-pyridylmethyl)-5-propyl-pyrazolo[3,4-d]pyrimidine-4,6(5H,7H)-dione A solution of 6-hydrazino-1-(3-pyridylmethyl)-3-propyluracil (0.7 g, 2.66 mM) and methyl isothiocyanate (0.7 ml, 10.3 mM) in DMF (10 ml) was heated at 90° C. for 14 hours and then at 110° C. for 14 hours. To the reaction solution was added 50% methanol (10 ml) and the mixture was cooled to give crystals. Recrystallization from DMF/ethanol/water afforded colorless needles (0.5 g, 60%), m.p. >300° C.

Elemental Analysis for $C_{15}H_{18}N_6O_2$:

|  | C (%) | H (%) | N (%) |
| --- | --- | --- | --- |
| Calcd.: | 57.31; | 5.77; | 26.73 |
| Found: | 57.20; | 5.60; | 26.92 |

Example-13

3-Methylamino-5-propyl-7-(2-thienylmethyl)-pyrazolo[3,4-d]pyrimidine-4,6(5H,7H)-dione A solution of 6-hydrazino-3-propyl-1-(2-thienylmethyl)uracil (1.8 g, 6.4 mM) and methyl isothiocyanate (1.36 ml, 20 mM) in DMF (30 ml) was stirred at 60° C. for 5 hours and then at 110° C. for 12 hours. To the solution was added methanol (10 ml) and the mixture was cooled to give crystals. Recrystallization from DMF/methanol afforded colorless crystals (0.9 g, 44%), m.p. >300° C.

Elemental Analysis for $C_{14}H_{17}N_5O_2S$:

|  | C (%) | H (%) | N (%) |
| --- | --- | --- | --- |
| Calcd.: | 52.65; | 5.36; | 21.93 |
| Found: | 52.66; | 5.02; | 21.96 |

Example-14

3-Methylamino-7-phenethyl-5-propylpyrazolo[3,4-d]-pyrimidine-4,6(5H,7H)-dione

A solution of 6-hydrazino-1-phenethyl-3-propyluracil (1.5 g, 5.2 mM) and methyl isothiocyanate (1.1 ml, 16 mM) in DMF (15 ml) was stirred at 60° C. for 2 hours and then at 120° C. for 15 hours. To the solution was added 50% methanol (10 ml) and the mixture was cooled to give crystals. Recrystallization from DMF/methanol afforded colorless crystals (0.7 g, 41%), m.p. 256°–258° C.

Elemental Analysis for $C_{17}H_{21}N_5O_2$:

|  | C (%) | H (%) | N (%) |
| --- | --- | --- | --- |
| Calcd.: | 62.37; | 6.47; | 21.39 |
| Found: | 62.40; | 6.03; | 21.64 |

Example-15

3-Methylamino-7-(3-phenylpropyl)-5-propyl-pyrazolo[3,4-d]pyrimidine-4,6(5H,7)-dione A solution of 6-hydrazino-1-(3-phenylpropyl)-3-propyluracil (1.7 g, 6.3 mM) and methyl isothiocyanate (0.8 ml, 12 mM) in DMF (20 ml) was stirred at 60° C. for 2 hours and then at 100° C. for 12 hours. To the solution was added methanol (10 ml) and the mixture was cooled to give crystals. Recrystallization from DMF/methanol afforded colorless needles (0.9 g, 47%), m.p. 267°–269° C.

Elemental Analysis for $C_{18}H_{23}N_5O_2$:

|  | C (%) | H (%) | N (%) |
| --- | --- | --- | --- |
| Calcd.: | 63.32; | 6.79; | 20.51 |
| Found: | 63.18; | 6.59; | 20.38 |

Example-16

7-(2-Benzyloxyethyl)-3-methylamino-5-propyl-pyrazolo[3,4-d]pyrimidine-4,6(5H,7H)-dione A solution of 1-(2-benzyloxyethyl)-6-hydrazino-3-propyluracil (2.0 g, 6.3 mM) and methyl isothiocyanate (1.2 ml, 18 mM) in DMF (20 ml) was stirred at 60° C. for 1 hour and then at 100° C. for 20 hours. To the solution was added 50% methanol (10 ml) and the mixture was cooled to give crystals. Recrystallization from DMF/methanol afforded colorless prisms (1.39 g, 62%), m.p. 224°-226° C.

Elemental Analysis for $C_{18}H_{23}N_5O_3$:

|  | C (%) | H (%) | N (%) |
|---|---|---|---|
| Calcd.: | 60.49; | 6.49; | 19.59 |
| Found: | 60.74; | 6.41; | 19.53 |

Example-17

7-Benzyl-2-butyryl-3-methylamino-5-propyl-2H-pyrazolo[3,4-d]pyrimidine-4,6(5H,7H)-dione A mixture of 7-benzyl-3-methylamino-5-propyl-pyrazolo[3,4-d]pyrimidine-4,6(5H,7H)-dione (0.7 g, 2.2 mM) and butyric anhydride (0.71 g, 4.5 mM) in pyridine (10 ml) was stirred at 60° C. for 24 hours. The reaction solution was concentrated to dryness and the residue was purified by chromatography on silica gel (20 g, chloroform). The crude crystals were recrystallized from acetone/isopropyl ether to give colorless needless (0.61 g, 71%), m.p. 138°-139° C.

Elemental Analysis for $C_{20}H_{25}N_5O_3$:

|  | C (%) | H (%) | N (%) |
|---|---|---|---|
| Calcd.: | 62.65; | 6.57; | 18.26 |
| Found: | 62.82; | 6.64; | 18.41 |

Example-18

2-Acetyl-7-(3-chlorobenzyl)-3-methylamino-5-propyl-2H-pyrazolo[3,4-d]pyrimidine-4,6(5H,7H)-dione A solution of 7-(3-chlorobenzyl)-3-methylamino-5-propylpyrazolo[3,4-d]pyrimidine-4,6(5H,7H)-dione (1.0 g, 2.9 mM) and acetic anhydride (1.0 ml, 9.8 mM) in pyridine (15 ml) was stirred at 80° C. for 5 hours. The solution was concentrated to dryness and the residue was triturated with water (10 ml). Recrystallization from chloroform/ether gave colorless needles (0.95 g, 85%), m.p. 169°-171° C.

Elemental Analysis for $C_{18}H_{20}ClN_5O_3$:

|  | C (%) | H (%) | N (%) |
|---|---|---|---|
| Calcd.: | 55.46; | 5.17; | 17.96 |
| Found: | 55.13; | 5.19; | 18.51 |

Example-19

7-(3-Chlorobenzyl)-2-isobutyryl-3-methylamino-5-propyl-2H-pyrazolo[3,4-d]pyrimidine-4,6(5H,7H)-dione A solution of 7-(3-chlorobenzyl)-3-methylamino-5-propylpyrazolo[3,4-d]pyrimidine-4,6(5H,7H)-dione (0.7 g, 2.0 mM) and isobutyric anhydride (1.0 ml, 6 mM) in pyridine (10 ml) was stirred at 80° C. for 5 hours. The solution was concentrated to dryness and the residue was triturated with water (10 ml). Recrystallization from chloroform/ether gave colorless needles (0.5 g, 59%), m.p. 154°-156° C.

Elemental Analysis for $C_{20}H_{24}ClN_5O_3$:

|  | C (%) | H (%) | N (%) |
|---|---|---|---|
| Calcd.: | 57.48; | 5.79; | 16.76 |
| Found: | 57.20; | 5.70; | 16.97 |

Example-20

7-(3-Chlorobenzyl)-2-methoxycarbonyl-3-methylamino-5-propyl-2H-pyrazolo[3,4-d]pyrimidine-4,6(5H,7H)-dione To a mixture of 7-(3-chlorobenzyl)-3-methylamino-5-propylpyrazolo[3,4-d]pyrimidine-4,6(5H,7H)-dione (1.0 g, 2.9 mM) and triethylamine (1.2 ml, 8.6 mM) in dioxane (50 ml) was added dropwise methyl chloroformate (0.66 ml, 8.5 mM) at room temperature and the mixture was allowed to stir at the same temperature for 20 hours. The mixture was concentrated to dryness and the residue was triturated with water (10 ml). Recrystallization from chloroform/methanol gave colorless crystals (1.0 g, 86%), m.p. 164°-166° C.

Elemental Analysis for $C_{18}H_{20}ClN_5O_4$:

|  | C (%) | H (%) | N (%) |
|---|---|---|---|
| Calcd.: | 53.27; | 4.97; | 17.26 |
| Found: | 53.44; | 4.91; | 17.43 |

Example-21

2-Butyryl-7-(3-chlorobenzyl)-3-methylamino-5-propyl-2H-pyrazolo[3,4-d]pyrimidine-4,6(5H,7H)-dione A mixture of 7-(3-chlorobenzyl)-3-methylamino-5-propylpyrazolo[3,4-d]pyrimidine-4,6(5H,7H)-dione (0.7 g, 2 mM) and butyric anhydride (0.64 g, 4 mM) in pyridine (10 ml) was stirred at 60° C. for 27 hours. The reaction solution was concentrated to dryness and the residue was purified by chromatography on silica gel (18 g, chloroform). Recrystallization from acetone/isopropyl ether gave colorless needles (0.63 g, 75%), m.p. 152°-153° C.

Elemental Analysis for $C_{20}H_{24}ClN_5O_3$:

|  | C (%) | H (%) | N (%) |
|---|---|---|---|
| Calcd.: | 57.48; | 5.79; | 16.76 |
| Found: | 57.45; | 5.78; | 16.64 |

Example-22

7-Benzyl-5-butyl-3-methylaminopyrazolo[3,4-d]pyrimidine-4,6(5H,7H)-dione

A solution of 1-benzyl-3-butyl-6-hydrazinouracil (4.0 g, 13.9 mM) and methyl isothiocyanate (2.85 ml, 41.7 mM) in DMF (50 ml) was stirred at 120° C. for 20 hours. To the solution was added methanol (20 ml) and the mixture was cooled to give crystals. Recrystallization from DMF/methanol gave colorless crystals (3.0 g, 66%), m.p. 282°-284° C.

Elemental Analysis for $C_{17}H_{21}N_5O_2$:

|  | C (%) | H (%) | N (%) |
|---|---|---|---|
| Calcd.: | 62.37; | 6.47; | 21.39 |
| Found: | 62.60; | 6.55; | 21.32 |

Example-23

7-Benzyl-5-butyl-3-dimethylaminopyrazolo[3,4-d]pyrimidine-4,6(5H,7H)-dione

To a solution of 1-benzyl-3-butyl-6-hydrazinouracil (1.0 g, 3.5 mM) in chloroform (30 ml) was added in portions phosgene iminium chloride (0.73 g, 4.5 mM) at room temperature and the mixture was stirred at 50° C. for 3 hours. The reaction solution was concentrated to dryness to give a brown syrup, which was purified by column chromatography on silica gel (30 g, chloroform) to give pale yellow crystals. Recrystallization from 80% ethanol gave colorless needles (0.61 g, 52%), m.p. 177°–179° C.

Elemental Analysis for $C_{18}H_{23}N_5O_2$:

|  | C (%) | H (%) | N (%) |
|---|---|---|---|
| Calcd.: | 63.32; | 6.79; | 20.51 |
| Found: | 63.39; | 6.89; | 20.43 |

Example-24

7-Benzyl-5-butyl-2-methyl-3-methylamino-2H-pyrazolo[3,4-d]pyrimidine-4,6(5H,7H)-dione A mixture of 7-benzyl-5-butyl-3-methylaminopyrazolo[3,4-d]pyrimidine-4,6(5H,7H)-dione (1.5 g, 4.58 mM), methyl iodide (0.48 ml, 6 mM) and potassium carbonate (0.82 g, 6 mM) was stirred at room temperature for 12 hours. The mixture was concentrated to dryness and the residue was extracted with chloroform and water. The organic layer was washed with water, dried (MgSO$_4$) and concentrated to dryness to give a solid. Recrystallization from 80% ethanol gave colorless needles (0.88 g, 50%), m.p. 146°–148° C.

Elemental Analysis for $C_{18}H_{23}N_5O_2$:

|  | C (%) | H (%) | N (%) |
|---|---|---|---|
| Calcd.: | 63.32; | 6.79; | 20.51 |
| Found: | 63.55; | 6.86; | 20.29 |

Example-25

5-Butyl-7-(4-methoxybenzyl)-3-methylaminopyrazolo[3,4-d]pyrimidine-4,6(5H,7H)-dione A solution of 3-butyl-6-hydrazino-1-(4-methoxybenzyl)-uracil (2.0 g, 6.3 mM) and methyl isothiocyanate (1.36 ml, 20 mM) in DMF (20 ml) was stirred at 120° C. for 20 hours. To the solution was added ethanol (20 ml) and the mixture was cooled to give crude crystals. Recrystallization from DMF/ethanol gave colorless crystals (1.2 g, 53%), m.p. 292°–294° C.

Elemental Analysis for $C_{18}H_{23}N_5O_3$:

|  | C (%) | H (%) | N (%) |
|---|---|---|---|
| Calcd.: | 60.49; | 6.49; | 19.59 |
| Found: | 60.58; | 6.49; | 19.54 |

Example-26

5-Butyl-7-(4-chlorobenzyl)-3-methylaminopyrazolo[3,4-d]pyrimidine-4,6(5H,7H)-dione A solution of 3-butyl-1-(4-chlorobenzyl)-6-hydrazinouracil (3.0 g, 9.3 mM) and methyl isothiocyanate (2.0 ml, 29 mM) in DMF (30 ml) was stirred at 120° C. for 20 hours. To the solution was added ethanol (20 ml) and the mixture was cooled to give crude crystals. Recrystallization from DMF/ethanol gave pale yellow crystals (1.91 g, 57%), m.p. 292°–294° C.

Elemental Analysis for $C_{17}H_{20}ClN_5O_2$:

|  | C (%) | H (%) | N (%) |
|---|---|---|---|
| Calcd.: | 56.43; | 5.57; | 19.36 |
| Found: | 56.51; | 5.49; | 19.22 |

Example-27

5-Butyl-3-methylamino-7-(2-nitrobenzyl)pyrazolo[3,4-d]pyrimidine-4,6(5H,7H)-dione A solution of 3-butyl-6-hydrazino-1,-(2-nitrobenzyl)uracil (4.0 g, 12 mM) and methyl isothiocyanate (2.4 ml, 36 mM) in DMF (40 ml) was stirred at 120° C. for 20 hours. To the solution was added ethanol (20 ml) and the mixture was cooled to give crystals. Recrystallization from DMF/ethanol gave colorless needles (2.0 g, 45%), m.p. >300° C.

Elemental Analysis for $C_{17}H_{20}N_6O_4$:

|  | C (%) | H (%) | N (%) |
|---|---|---|---|
| Calcd.: | 54.83; | 5.41; | 22.57 |
| Found: | 54.89; | 5.31; | 22.43 |

Example-28

5-Butyl-3-methylamino-7-(4-nitrobenzyl)pyrazolo[3,4-d]pyrimidine-4,6(5H,7H)-dione A solution of 3-butyl-6-hydrazino-1-(4-nitrobenzyl)uracil (1.7 g, 5 mM) and methyl isothiocyanate (0.7 ml, 10 mM) in DMF (20 ml) was stirred at 120° C. for 20 hours. To the solution was added ethanol (20 ml) and the mixture was cooled to give crystalline product. Recrystallization from DMF/ethanol gave pale yellow crystals (0.61 g, 32%), m.p. 277°–279° C.

Elemental Analysis for $C_{17}H_{20}N_6O_4$:

|  | C (%) | H (%) | N (%) |
|---|---|---|---|
| Calcd.: | 54.83; | 5.41; | 22.57 |
| Found: | 54.80; | 5.11; | 22.51 |

Example-29

5-Butyl-3-methylamino-7-(2-benzylaminoethyl)-pyrazolo[3,4-d]pyrimidine-4,6(5H,7H)-dione A mixture of 5-butyl-7-(2-chloroethyl)-3-methylaminopyrazolo[3,4-d]pyrimidine-4,6(5H,7H)- dione (0.6 g, 2 mM) and benzylamine (0.66 ml, 6 mM) in dioxane (20 ml) was refluxed for 20 hours. The reaction solution was concentrated to dryness under reduced pressure to give a syrup, which was poured onto ice-water to give colorless crystals. The crystls were dissolved in 1N-HCl and insoluble material was filtered off, followed by addition of 1N-ammonia water to give crystals. Recrystallization from DMF/methanol/water afforded colorless needles (0.32 g, 43%), m.p. 198°–200° C.

Elemental Analysis for $C_{19}H_{26}N_6O_2$:

|  | C (%) | H (%) | N (%) |
|---|---|---|---|
| Calcd.: | 61.60; | 7.08; | 22.69 |
| Found: | 61.51; | 6.87; | 22.58 |

Example-30

7-(2-benzyloxyethyl)-5-butyl-3-methylaminopyrazolo[3,4-d]pyrimidine-4,6(5H,7H)-dione A solution of 1-(2-benzyloxyethyl)-3-butyl-6-hydrazinouracil (2.1 g, 6.3 mM) and methyl isothiocyanate (1.36 ml, 20 mM) in DMF (20 ml) was stirred at 120° C. for 20 hours. To the solution was added 50% methanol (20 ml) and the mixture was cooled to give crystals. Recrystallization from DMF/methanol/water gave pale yellow crystals (0.94 g, 40%), m.p. 214°–216° C.

Elemental Analysis for $C_{19}H_{25}N_5O_3$:

|  | C (%) | H (%) | N (%) |
|---|---|---|---|
| Calcd.: | 61.44; | 6.78; | 18.85 |
| Found: | 61.42; | 6.53; | 19.09 |

Example-31

5-butyl-3-ethylamino-7-(4-methoxybenzyl)-pyrazolo[3,4-d]pyrimidine-4,6(5H,7H)-dione A solution of 3-butyl-6-hydrazino-1-(4-methoxybenzyl)uracil 0.64 g, 2 mM) and ethyl isothiocyanate (0.53 ml, 6 mM) in DMF (6 ml) was stirred at 90° C. for 14 hours and then at 110° C. for 14 hours. To the solution was added water (2 ml) and the mixture was cooled to give crystals. Recrystallization from DMF/ethanol/water gave colorless needles (0.52 g, 70%), m.p. 234°–236° C.

Elemental Analysis for $C_{19}H_{25}N_5O_3$:

|  | C (%) | H (%) | N (%) |
|---|---|---|---|
| Calcd.: | 61.44; | 6.78; | 18.86 |
| Found: | 61.35; | 6.93; | 18.77 |

Example-32

7-(4-aminobenzyl)-5-butyl-3-methylaminopyrazolo[3,4-d]pyrimidine-4,6(5H,7H)-dione hydrochloride To a suspension of 5-butyl-3-methylamino-7-(4-nitrobenzyl)pyrazolo[3,4-d]pyrimidine-4,6(5H,7H)-dione (1 g, 2.6 mM) in concentrated hydrochloric acid (5 ml) and ethanol (2.5 ml) was added dropwise a solution of stannous chloride (3.75 g) in ethanol (5 ml) at room temperature with stirring. The mixture was stirred at room temperature for 24 hours and concentrated to dryness. The residue was crystallized from hot water to give yellow crystals (0.42 g, 46%), m.p. >310° C.

Elemental Analysis for $C_{17}H_{22}N_6O_2 \cdot HCl \cdot \frac{1}{2}H_2O$

|  | C (%) | H (%) | N (%) |
|---|---|---|---|
| Calcd.: | 52.64; | 6.24; | 21.67 |
| Found: | 52.48; | 5.73; | 21.35 |

Formulation Example

When the compound (I) of the present invention is used as a therapeutic and prophylactic drug, it can be administered, for example, in the following prescription.

1. Tablet:

| (1) 7-(3-chlorobenzyl)-3-methylamino-5-propylpyrazolo-[3,4-d]pyrimidine-4,6(5H,7H)-dione | 20 mg |
|---|---|
| (2) lactose | 35 mg |
| (3) corn starch | 150 mg |
| (4) microcrystalline cellulose | 30 mg |
| (5) magnesium stearate | 5 mg |
|  | 240 mg |

The above ingredients (1), (2), (3), ⅔ of (4) and ½ of (5) are mixed and granulated. To the granules are added respective balances of (4) and (5), and the mixture is molded by compression into tablets.

2. Capsule:

| (1) 7-benzyl-3-methylamino-5-propylpyrazole[3,4-d]pyrimidine-4,6(5H,7H)-dione | 20 mg |
|---|---|
| (2) lactose | 100 mg |
| (3) microcrystalline cellulose | 70 mg |
| (4) magnesium stearate | 10 mg |
|  | 200 mg |

The above ingredients (1), (2), (3) and ½ of (4) are mixed and granulated. To the granules is added the balance of (4), and the mixture is put in a gelatin capsule.

Biological Experiment

Experiment 1

The nootropic action of the compound (I) was studied using a passive avoidance task. The apparatus consisted of light and dark chambers. Five-week old male mice were placed first in the light chamber. When the animals entered the dark chamber, an unescapable electric shock (0.5 mA, 3 sec.) was applied to them through the grid floor. These animals retained for several weeks the memory that they received the electric shock. This memory retention was disrupted by the following procedure, and the effect of the compound (I) of the present invention was tested. The mice, after they were subjected to an electric shock, were placed in a 4l-glass vessel filled with carbon dioxide gas. When the respiration was arrested, the animals were taken out and allowed to recover by applying artificial respiration. Then, the mice lost the memory of this experience of an electric shock.

On the following day, a retention recovery test was conducted. The mice were again placed in the light chamber of the passive avoidance apparatus and the time until the animals moved into the dark chamber was measured. These animals exposed to carbon dioxide gas usually moved again into the dark chamber in 10-20 sec. On the other hand, the mice administered with the compound (I) of the present invention recovered the memory, and they would not move into the dark chamber or took a long time before they moved there. The effect of this test compound was examined by comparing the average value (8 animals/group) of the period of time during which the mice stayed in the light chamber with that of the control group (administered with only a suspension of 5% gum arabic containing no test compound). The results were expressed by percent change rate relative to the mean value (100) in the control group. The test compounds were intraperitoneally administered 30 minutes before testing or orally administered 60 minutes before testing, as a suspension in 5% gum arabic solution.

Table 1 shows ameliorative effects of typical ones among the compounds (I) of the present invention on retention deficit of passive avoidance by exposure to carbon dioxide.

TABLE 1

| Ameliorative Effects on Retention Deficit | |
|---|---|
| Example No. | Amelioration rate (%) |
| Dosage (mg/kg, i.p.) | |
| 4 | 5 | 228* |
| | 20 | 345* |
| 6 | 5 | 267* |
| | 20 | 394* |
| 14 | 20 | 326* |
| 21 | 20 | 291* |
| 24 | 20 | 273* |
| 25 | 5 | 160 |
| | 20 | 233* |
| 26 | 20 | 266* |
| 27 | 20 | 410* |
| Dosage (mg/kg, orally) | |
| 6 | 20 | 304* |
| 8 | 20 | 236* |

*statistically significant difference ($p < 0.05$)

Experiment 2

Male Wistar rats well trained in a 8-arm radial maze were used. The symmetrical 8-arm maze consisted of 80 cm-arms projecting from a center platform, each arm being equipped with a food cup contained a pellet. The food deprived rat was placed in the center platform and allowed to choose 4 arms freely. The rat was removed from the apparatus immediately after the fourth choice and returned to its home cage. Following variable delay intervals, the rat was replaced in the center platform and allowed to continue the performance. The number of correct responses during the fifth to eighth choice (choices of arms which had not been visited earlier) and total errors (the number of arms revisited) were recorded. If the delay was less than 4 hours, the rate showed an increase in the number of correct responses and decrease in total errors. In the present study, the rat was removed from the apparatus immediately after the fourth choice, and given scopolamine (0.5 mg/kg, i.p.) and test compound (10 mg/kg, i.p.) simultaneously. One hour later, the rat was replaced on the apparatus and allowed to continue the performance. Seven to 12 rats per group were used.

As shown in Table 2, spatial memory of the rat was markedly disturbed by scopolamine as demonstrated by a decrease in correct responses and increase in total errors. The compound obtained from example 6 (compound 6) improved spatial memory deficit produced by scopolamine, and a significant increase in correct responses and decrease in total errors were observed.

TABLE 2

| Improving action on scopolamine-induced spatial memory deficit in the radial maze task | | | | |
|---|---|---|---|---|
| compound | dosage (mg/kg, i.p.) | correct responses | total errors | number of animals |
| saline | — | 3.3 ± 0.2 | 1.3 ± 0.4 | 12 |
| scopolamine saline | 0.5 — | 2.3 ± 0.2* | 3.0 ± 0.4* | 12 |
| scopolamine compound 6 | 0.5 10 | 2.9 ± 0.3 | 1.6 ± 0.4 | 7 |

Each value represents mean ± SE.
*statistically significant difference from saline control ($P < 0.01$)
  statistically significant difference from scopolamine control
    statistically significant difference from scopolamine control ($P < 0.05$)

Experiment 3

Male Wistar rats removed bilateral olfactory bulbs by suction were used. Each rat was placed on a platform (30×7×4.5 cm) located one side of a large cage (30×30×30 cm) equipped with the grid floor. When the rat stepped off the platform, it received an electric shock (0.6 mA, for 1 sec.). The rat was then returned to its home cage for 1 minute after which it was given a second trial. This procedure was repeated until the animal remained on the platform for 180 seconds without stepping off or until 10 trials had been given. At each trial, the time of step down was recorded. Eight to 10 rats per group were used, and the test compound was administered intraperitoneally 1 hour before the start of testing.

Table 3 shows the number of trials to the criterion of avoidance for 180 seconds on the platform. Olfactory bulbectomized control rats given saline exhibited a significant increase in the number of trials to the criterion compared with the sham-operated rats. Compound 6 produced a marked and significant improvement in acquisition of passive avoidance in bulbectomized rats.

TABLE 3

| Improving action on passive avoidance deficit in olfactory bulbectomized rats | | | | |
|---|---|---|---|---|
| Rats | compound | Dosage (mg/kg, i.p.) | number of trials | number of animals |
| sham-operated rats | saline | — | 3.5 | 10 |
| olfactory bulbectomized rats | saline | — | 7.7* | 8 |
| | compound 6 | 20 | 4.1 | 8 |

*statistically significant difference from sham-operated rats ($P < 0.01$)
  statistically significant difference from olfactory bulbectomized control rats ($P < 0.01$)

What is claimed is:
1. A compound of the formula (I)

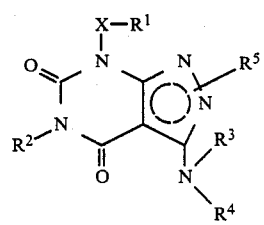

wherein

R¹ is phenyl, naphthyl, furyl, pyridyl, pyridinio, or thienyl which may be substituted by a member selected from the class consisting of halogen, $C_{1-4}$alkyl, $C_{1-4}$alkoxy, nitro, amino, N-$C_{1-4}$alkylamino, N,N-di$C_{1-4}$alkylamino, hydroxy, trifluoromethyl, carbamoyl, N-$C_{1-4}$alkylcarbamoyl and N,N-di$C_{1-4}$alkylcarbamoyl;

R² is $C_{1-4}$alkyl;

R³ and R⁴ are independently hydrogen or $C_{1-4}$alkyl;

R⁵ is hydrogen, $C_{1-2}$alkyl, $C_{1-5}$alkanoyl or $C_{1-4}$alkoxycarbonyl, the group R⁵ being attached at the 1- or 2-position of the pyrazole ring;

X is $C_{1-7}$alkylene or a group of the formula:
—$(CH_2)_m$—Y—$(CH_2)_n$— wherein m is 2 or 3,
n is an integer of 0 to 3,
and Y is oxygen, sulfur, imino or N-$C_{1-4}$alkylimino; and the dotted line designates the presence of two double bonds in the pyrazole ring or a pharmaceutically acceptable salt thereof.

2. A compound according to claim 1, wherein R¹ is phenyl, pyridyl, or thienyl which may be substituted by a member selected from the class consisting of halogen, $C_{1-4}$alkyl, $C_{1-4}$alkoxy, nitro, and amino.

3. A compound according to claim 1, wherein R¹ is phenyl which may be substituted by a member selected from the class consisting of halogen and nitro.

4. A compound according to claim 1, wherein R² is propyl or butyl.

5. A compound according to claim 1, wherein R³ is methyl or ethyl and R⁴ hydrogen.

6. A compound according to claim 1, wherein R⁵ is hydrogen or $C_{2-4}$alkanoyl.

7. A compound according to claim 1, wherein R⁵ is hydrogen.

8. A compound according to claim 1, wherein X is methylene or ethylene.

9. A compound according to claim 1,
wherein
R¹ is phenyl, which may be substituted by a member selected from the class consisting of halogen and nitro;
R² is propyl or butyl;
R³ is methyl;
R⁴ is hydrogen;
R⁵ is hydrogen or $C_{2-4}$alkanoyl attached at the 2-position of the pyrazole ring; and
X is methylene or ethylene or a pharmaceutically acceptable salt thereof.

10. A pharmaceutically acceptable salt according to claim 1, which is a pharmaceutically acceptable acid addition salt.

11. The compound according to claim 1, which is 7-benzyl-3-methylamino-5-propylpyrazolo[3,4-d]pyrimidine-4,6(5H,7H)-dione.

12. The compound according to claim 1, which is 7-(3-chlorobenzyl)-3-methylamino-5-propyl-pyrazolo[3,4-d]pyrimidine-4,6(5H,7H)-dione.

13. The compound according to claim 1, which is 7-(4-chlorobenzyl)-3-methylamino-5-propyl-pyrazolo[3,4-d]pyrimidine-4,6(5H,7H)-dione.

14. The compound according to claim 1, which is 3-methylamino-7-phenethyl-5-propylpyrazolo[3,4-d]pyrimidine-4,6(5H,7H)-dione.

15. The compound according to claim 1, which is 2-butyryl-7-(3-chlorobenzyl)-3-methylamino-5-propyl-2H-pyrazolo[3,4-d]pyrimidine-4,6(5H,7H)-dione.

16. The compound according to claim 1, which is 5-butyl-3-methylamino-7-(2-nitrobenzyl)pyrazolo[3,4-di]pyrimidine-4,6(5H,7H)-dione.

17. A pharmaceutical composition which comprises
(a) as the active ingredient, an amount effective to treat or prevent neurosis or dementia caused by cerebral apoplexy, head trauma or encephalatrophic diseases of a compound as claimed in claim 1 or a pharmaceutically acceptable salt thereof and
(b) a pharmaceutically acceptable carrier, vehicle or diluent therefor.

18. A pharmaceutical composition which comprises
(a) as the active ingredient, an amount effective to treat or prevent dementia caused by cerebral apoplexy, head trauma or encephalatrophic diseases of a compound as claimed in claim 1 or a pharmaceutically acceptable salt thereof and
(b) a pharmaceutically acceptable carrier, vehicle or diluent therefor.

* * * * *